United States Patent [19]
Lorincz et al.

[11] 4,424,559
[45] Jan. 3, 1984

[54] MODULAR INSTRUMENTATION FOR MONITORING AND CONTROL OF BIOCHEMICAL PROCESSES

[75] Inventors: Robert S. Lorincz, Milltown; Carmine Masucci, Piscataway; Daniel N. Bull, Upper Montclair, all of N.J.

[73] Assignee: New Brunswick Scientific Co., Inc., Edison, N.J.

[21] Appl. No.: 238,737

[22] Filed: Feb. 27, 1981

[51] Int. Cl.$^3$ .............................................. G06F 15/46
[52] U.S. Cl. ................................... 364/131; 364/188; 364/172; 364/138; 364/500; 422/62; 435/3; 435/290
[58] Field of Search ........................ 364/130, 131–136, 364/140–147, 188, 189, 200 MS File, 900 MS File, 496, 497, 500–502, 138, 139, 172–175; 422/62, 67; 435/3, 289, 290, 813

[56] References Cited

U.S. PATENT DOCUMENTS

| | | | |
|---|---|---|---|
| 4,001,557 | 1/1977 | Stephenson | 364/143 |
| 4,064,394 | 12/1977 | Allen | 364/200 X |
| 4,178,634 | 12/1979 | Bartlett | 364/900 |
| 4,200,916 | 4/1980 | Seipp | 364/900 |
| 4,215,398 | 7/1980 | Burkett et al. | 364/141 X |
| 4,344,127 | 8/1982 | McDaniel et al. | 364/130 |

FOREIGN PATENT DOCUMENTS 2041572 9/1980 United Kingdom .
WO80/00383 3/1980 PCT Int'L Appl. .

OTHER PUBLICATIONS

J. Gallacher, Industrial Data Acquisition and Control Systems, Jun., 1979, vol. 3, No. 5, *Microprocessors and Microsystems*, pp. 210–218.

Primary Examiner—Joseph F. Ruggiero
Attorney, Agent, or Firm—Blum, Kaplan, Friedman, Silberman & Beran

[57] ABSTRACT

A modular instrumentation system for monitoring and control of biochemical processes, and in particular of fermentation processes is provided. The system includes a plurality of function monitoring and control modules each including a microprocessor and associated memory devices, manual input devices and an interface for the receipt of sensor signals and the transmission of control signals. The modules for a plurality of functions have substantially common design and are adapted for relatively quick conversion to another function. The system may include an instrument console adapted to receive a plurality of the function monitoring and control modules as well as incorporating provision for sensor inputs, power inputs, one or more recorders, one or more pumps and/or an interface for an external computer. The back plane of the console is provided with a conductor array interconnecting the various modules, power supply, pumps, recorders, sensor inputs and external computer interface and incorporates provision for the plug-in connection of the respective modules therewith.

66 Claims, 14 Drawing Figures

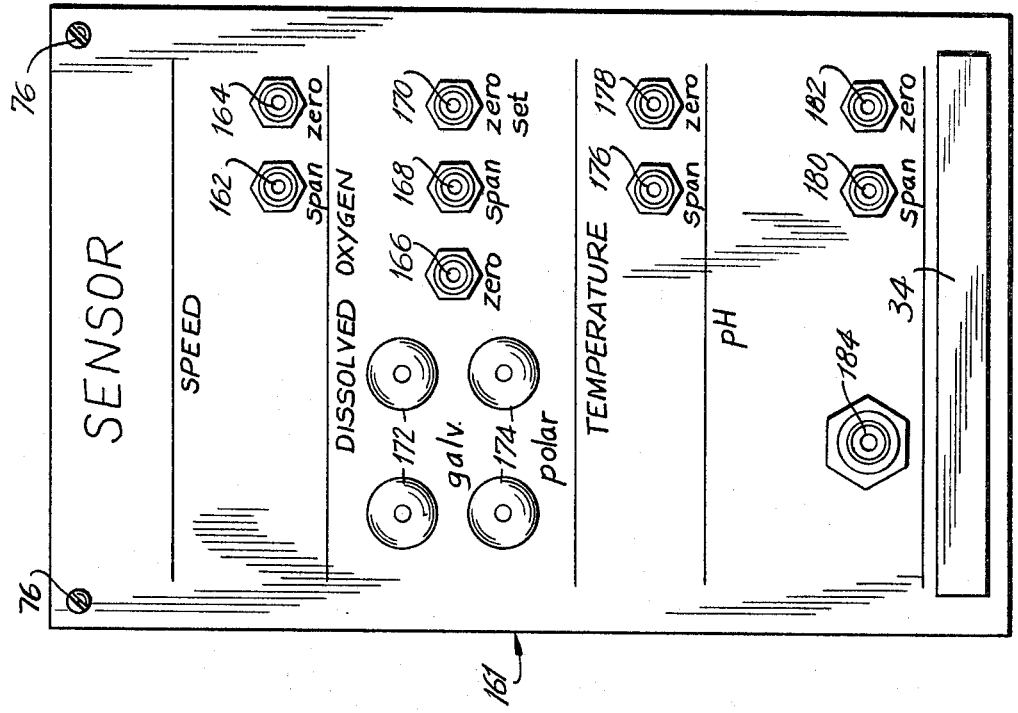
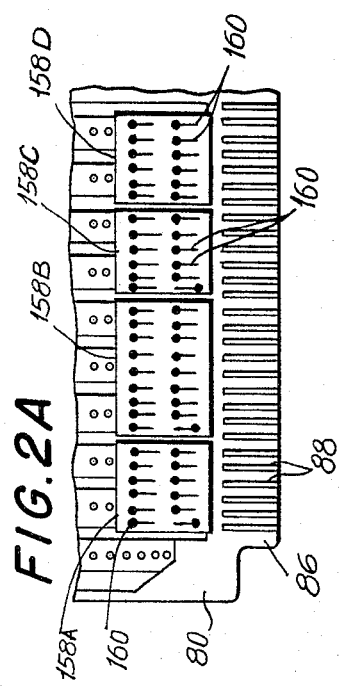
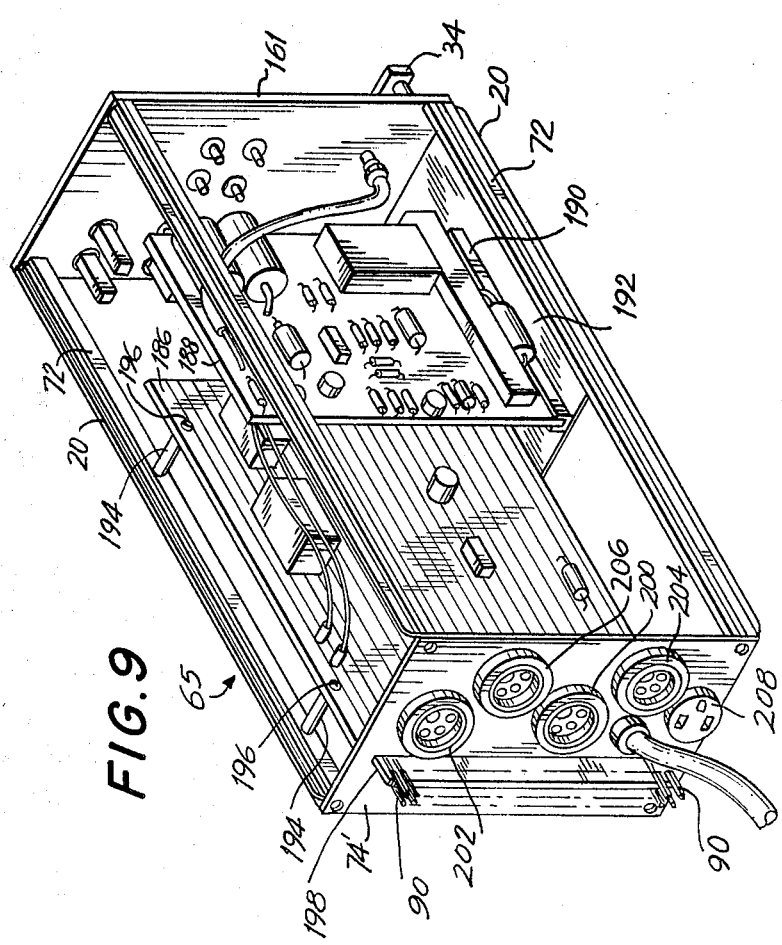

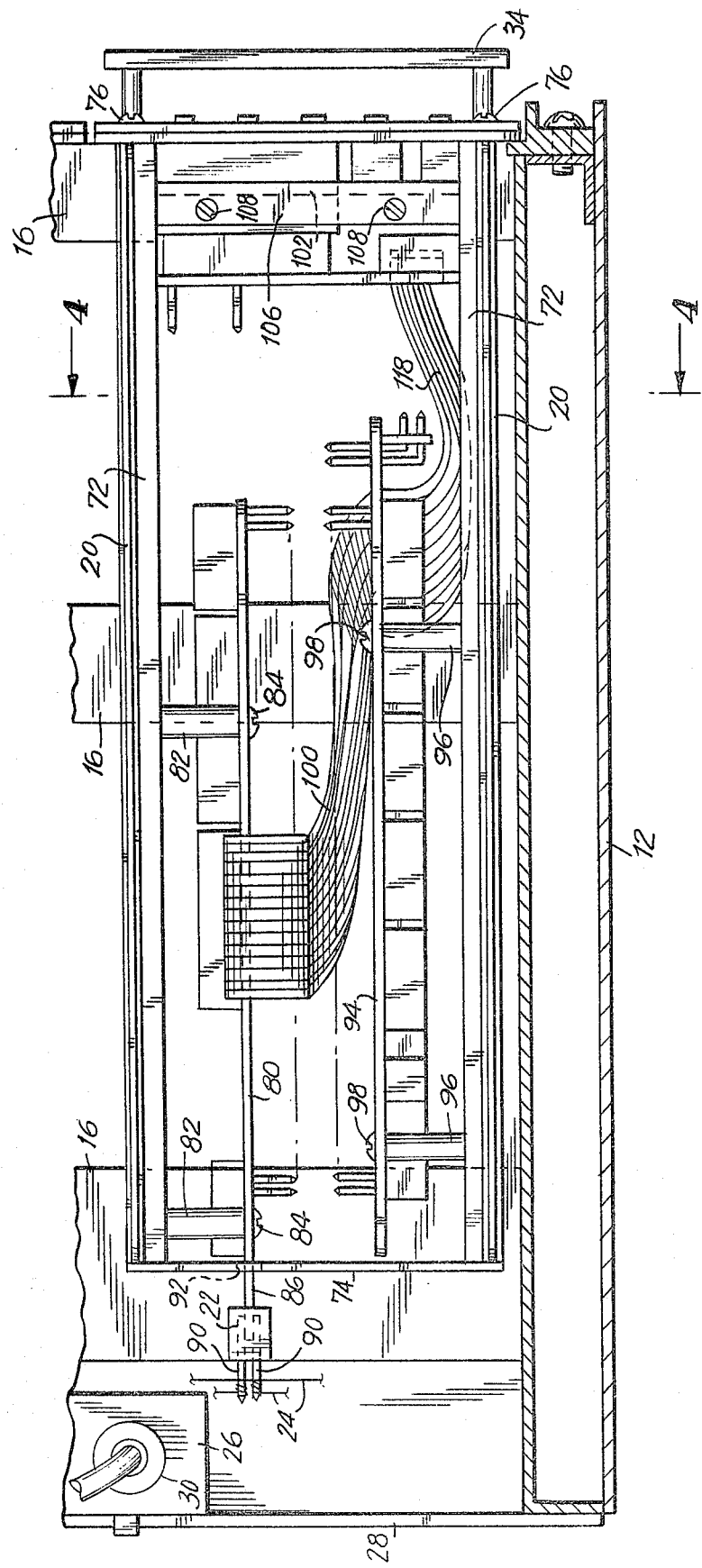

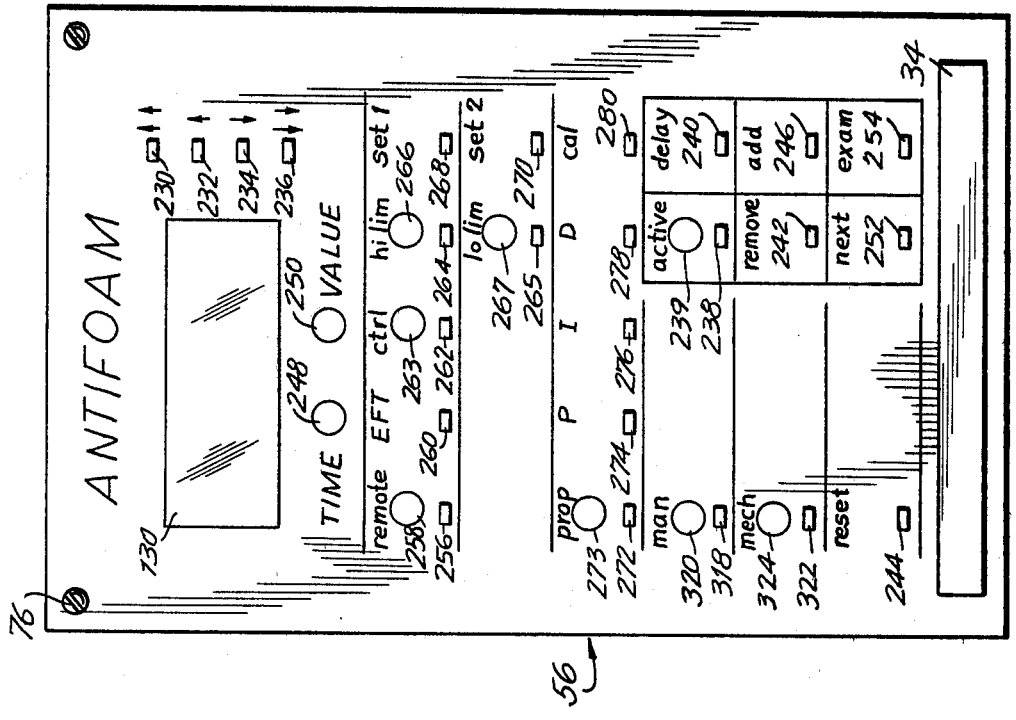
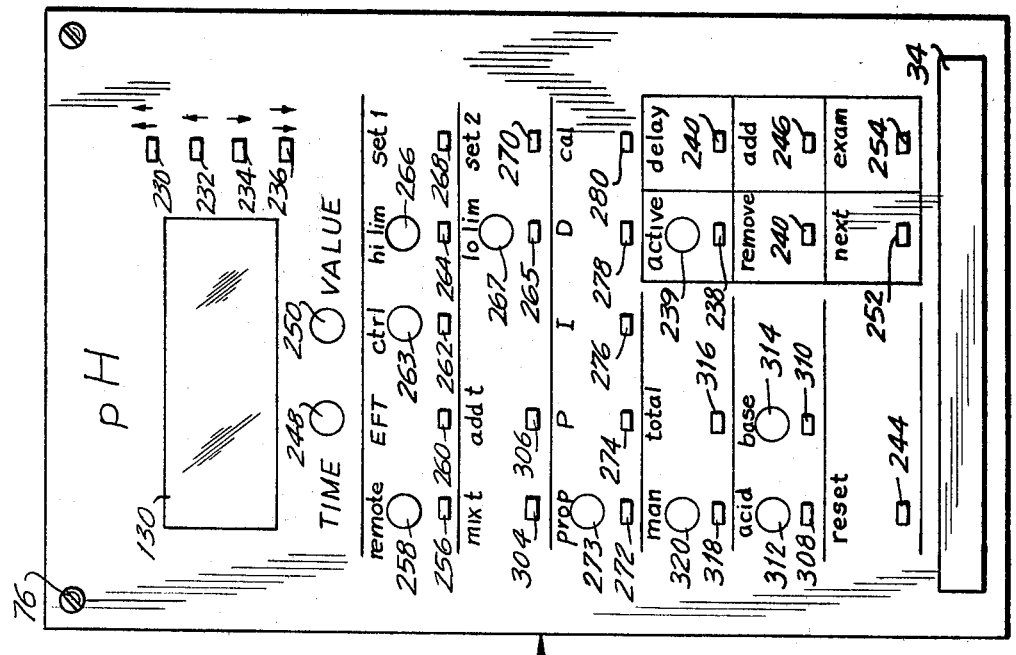

MODULAR INSTRUMENTATION FOR MONITORING AND CONTROL OF BIOCHEMICAL PROCESSES

BACKGROUND OF THE INVENTION

This invention is directed to the monitoring and control of biochemical processes, and in particular, of fermentation processes. Biochemical processes are, in general, relatively slow yet complex. The processes are greatly affected by environmental factors and such processes have long been contolled by adjustments in temperature, pressure, speed of agitation, pH, sparge air flow, nutrient feed and other factors. The control of these environmental factors and in particular the interactive control thereof has been the subject of substantial research effort. In U.S. Pat. Nos. 3,926,737 and 3,926,738, issued on Dec. 16, 1975 to Wilson et al. and assigned to the assignee hereof, a method and apparatus is taught for control of biochemical processes based on the detection of the values of selected controllable and dependent variables, the calculation by means of a computer of at least one further, not directly measurable dependent variable on a real-time, on-line basis from the plurality of selected controllable and dependent variables, the not directly measurable dependent variable being representative of the stage of the biochemical process, and thereafter interactively regulating the values of the controllable variables in response to the calculated values of the further dependent variable to bring the further dependent variable to predetermined levels to create the desired environmental conditions for the biochemical process. While this method and apparatus for control of biochemical processes represents an effective and highly sophisticated technique for the control thereof, it is frequently desirable, particularly in connection with laboratory fermentors, to monitor and control the various controllable variables directly along predetermined and alterable profiles, which profiles can be interactively controlled. This has lead to the development of various forms of monitoring and control devices including various "modular" instrumentation packages. Where such systems are controlled exclusively through a central computer, then the failure of the computer generally leads to the loss of the process. On the other hand, the existing "modular" instrument monitoring and control arrangements lack the flexibility for complete monitoring and control. To the extent that such prior instrumentation modules are hard wired, they are difficult to change. Further, the various function modules are generally not readily interchangeable necessitating the maintenance of extensive spare components if the process is to be saved despite the failure of a particular "module".

By providing function monitoring and control modules which are capable of plug-in coupling to a console which includes central power supply, sensor input and recording devices and may further include a central computer interface, by providing each such module with its own microprocessor for control and operation thereof as well as manual input means and, if desired, a display, and by making said modules substantially interchangeable with readily accomplished modifications, the foregoing disadvantages in the prior art arrangements are overcome.

SUMMARY OF THE INVENTION

Generally speaking, in accordance with the invention, modular instrumentation for the monitoring and control of biochemical processes is provided, including a function monitoring and control module having a microprocessor, first memory means cooperating with said microprocessor for storing the program for the operation of said module, a second electrically alterable memory means for storing at least function set point data, manual input means for inputting said set point data and for selectively controlling the operation of said module, and interface means for at least receiving signals representative of sensor output and transmitting signals for effecting function control. Said module may include display means for cooperation with said manual input means for effecting set point input and module control and for displaying monitored function data.

A plurality of said modules may be provided in a system including instrument console means, said instrument console means including a cabinet adapted for the removable mounting of said module and including power source means, sensor signal receiving means, control signal transmitting means and a conductive array interconnecting said module, said power source means, said sensor signal receiving means and said control signal transmitting means, each of said modules being releasably plugable into said conductive array. Said console may further include recorder means interconnected to said conductive array for receiving and recording data representative of monitored functions from selected ones of said function modules. Said console means may further include pump means interconnected to said conductor array for receiving control signals from a selected one of said modules for the operation thereof. The console means may also include a sensor module means including conditioning circuit means for placing received sensor signals into a form usable by said function modules and for placing control signals transmitted by said function module into a form effective for the control of the function. The console means may also include computer interface means coupled to said conductor array for permitting transmission of data to said function modules for the setting of set points and control thereof.

Each of said function modules may be adapted for interchangeability upon the substitution of at least the first memory means thereof. Said function modules may include means for connection to selected channels of said conductive array and for the substitution of the manual input means, together with the substitution of said first memory means for effecting the interchangeability of said function modules.

Accordingly, it is an object of the instant invention to provide modular instrumentation for the control and monitoring of biochemical processes, and in particular, of fermentation processes.

Another object of the invention is to provide control and monitoring function modules which may be readily interchanged through relatively simple modifications.

A further object of the invention is to provide modular instrumentation for the monitoring and control of biochemical processes which permits the complete manual inputting of a profile of each function and the separate, yet interactive setting and control of these functions.

A still further object of the invention is to provide modular instrumentation for the control and monitoring of biochemical processes which is compact and easy to use, yet provides a full range of controls including PID controls for each function.

A still further object of the invention is to provide modular instrumentation for the control of biochemical processes wherein each module incorporates a separate microprocessor for the operation thereof.

Still other objects and advantages of the invention will in part be obvious and will in part be apparent from the specification and drawings.

The invention accordingly comprises the features of construction, combinations of elements, and arrangements of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 2A is a fragmentary top plan view of the I/O board showing the channel selection arrangement;

FIG. 3 is a sectional view taken along lines 3—3 of FIG. 2 with portions of the module support omitted, showing a top view of the temperature module;

FIG. 7 is a view of the front panel of a pH module in accordance with the invention;

FIG. 8 is a view of a front panel of an antifoam module in accordance with the invention;

FIG. 9 is a rear perspective view of the sensor module in accordance with the invention;

FIG. 10 is a view of the front panel of the sensor module in accordance with the invention;

DESCRIPTION OF THE PREFERRED EMBODIMENTS

Figure 1:
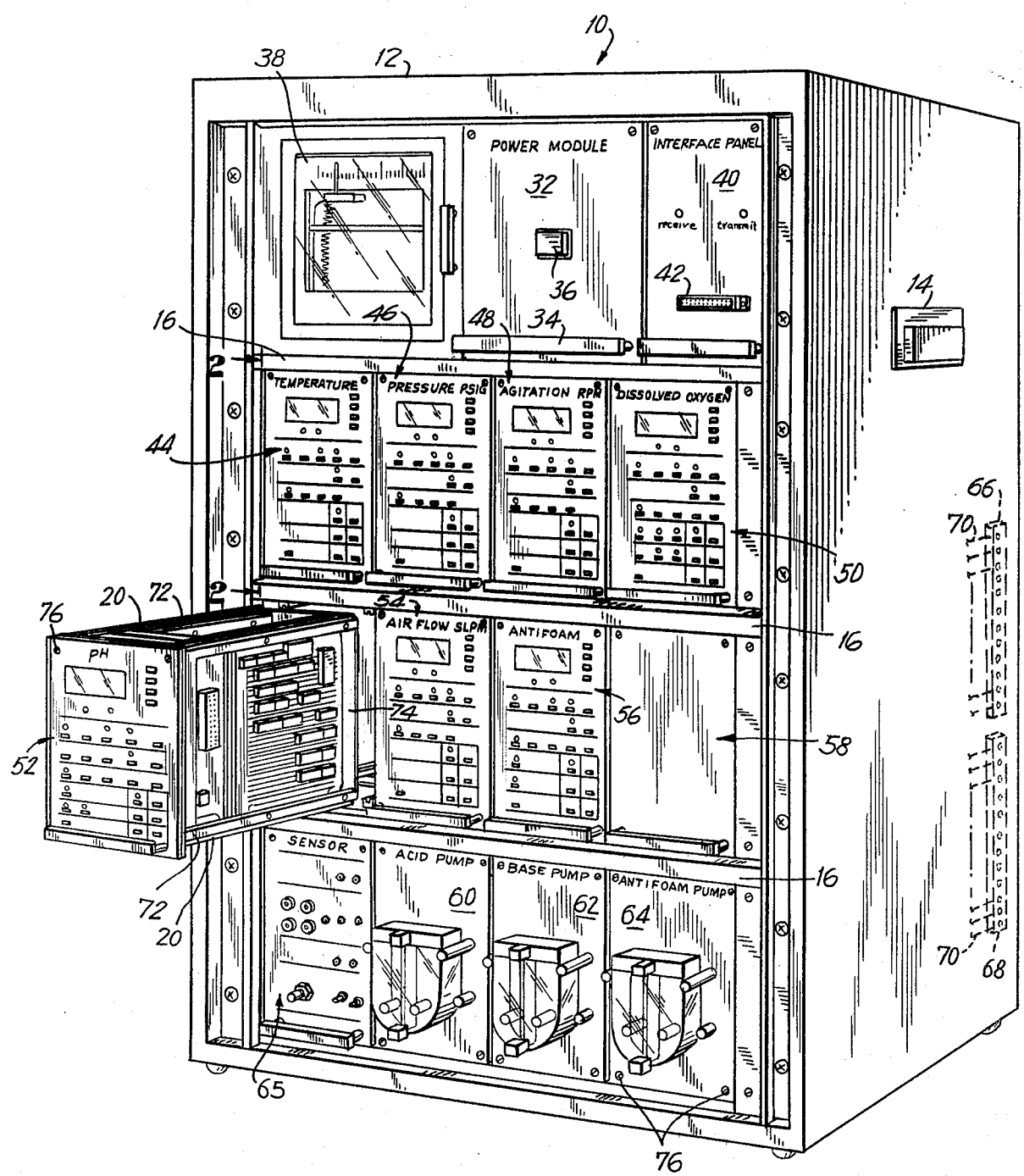
FIG. 1 is a front perspective view of an instrument console in accordance with the invention with one module removed therefrom.

Referring to FIGS. 1-4, one embodiment of an instrument console 10 is depicted including a housing 12 of conventional design, adapted to releasably support a plurality of modules as more particularly described below. In order to appreciate the size of instrument console 12, in one embodiment, the housing is about 19 inches in width, 21 inches in depth and 28 inches in height. The console is relatively compact when the scope of the monitoring and control functions performed thereby are considered. The housing is provided with a pair of hand grips 14 in the side walls thereof to facilitate carrying thereof. The housing 12 is provided with three intermediate shelves 16 formed of an open grid to permit the circulation of air for the cooling of the various electrical components therein. A plurality of rails 18 are mounted on the top and bottom surfaces of shelves 16 and on the inside surfaces of the top and bottom walls of housing 12 positioned to receive, guide and support upwardly and downwardly projecting ribs 20 formed in the frame of each module mounted within housing 12. The rails 18 extend from the front to the rear of the housing to permit the displacement in and out of the housing of the respective modules as discussed more particularly below.

The rear of the housing supports a back plane consisting of a plurality of socket members 22 extending vertically and positioned to the rear of each module and an array of conducted leads 24 which interconnect the respective sockets 22 and which are connected to the various elements of the instrument console as will be more particularly described below. In one embodiment, the array is provided with one hundred conductive leads with each socket 22 providing one hundred pin connections. In an alternate embodiment (not shown) the leads 24 may be replaced by a printed circuit conductive array as is well known in the art. Also mounted to the rear of the housing 12 is a socket 26 supported on a shelf 28 which permits coupling of the console to an external source of power through plug 30, socket 26 being coupled to a power module 32 through conductive array 24. Said power module may be manipulated into and out of housing 12 by means of handle 34. Power module 32 is positioned in registration with a socket 22 (not shown) and is provided with a corresponding plug and formed from the edge of a circuit board as described below. Power module 32 is adapted to provide, on various channels of the multichannel conductive array 24, the desired voltages required for the operation of the console system. A push-button switch 36, preferably provided with an on-indicating light therein, serves to turn the power supply, and therefore the entire console, on and off. All of the elements of the console are driven from the voltages generated at the power module and transmitted along the conductive array.

Also received within housing 12 is a recorder module 38 consisting, in one embodiment, of a conventional six channel strip chart recorder. In this embodiment, up to two such recorders may be provided, twelve channels being alotted to the recorder function. In addition to the power module and recorder module, the top row of the instrument console includes an interface panel 40 intended to provide interconnection with an external computer through socket 42 mounted on the front panel of module 40. The operation of interface module 40 is more particularly described below. Interface module 40 is provided with two LED indicator lights indicative of whether the console is receiving or transmitting data to the external computer. The interface panel provides interconnection between data lines forming a part of the conductive array 24 and the external computer.

The embodiment of the instrument console 10 depicted incorporates seven function modules, namely temperature module 44, pressure module 46, agitation (speed) module 48, dissolved oxygen module 50, pH module 52, air flow module 54 and antifoam module 56. This particular console has provision for one additional module for performing a desired function such as nutrient or precursor input control through control of pumps in response to load cells or the like, or redox control through the control of application of oxidation and reduction agents. The function modules occupy the two middle shelves.

The bottom shelf is provided with three pump modules, acid pump module 60 and base pump module 62 for control by pH module 52, and antifoam pump module 64 for control by antifoam module 56. In addition, a sensor module 65 is provided (see FIG. 9), incorporating conditioning circuitry for conditioning the function module control signals to operate certain controls and for conditioning certain sensor input signals for application to the function modules. The operation of the sensor module will be discussed in greater detail below. Additional sensor inputs and control outputs, where conditioning is not required, may be made by means of terminal blocks 66 and 68 mounted on the inside surface of one side wall of housing 12. Said terminal blocks are coupled by lines 70 to selected channels of the conductive array 24. Terminal blocks 66 and 68 also serve as output connections to external alarm devices such as buzzers as will be more particularly described below.

Each of the modules discussed above incorporates a frame having four corner supports 72 extending from front to back and supported between a front panel and a rear wall 74. The frame is held together by screws 76 and by the screws (not shown) holding the respective handles 34 of the respective modules in position. Each of the corner supports is formed with one of the upwardly or downwardly projecting ribs 20 which ride in rails 18.

Figure 2:
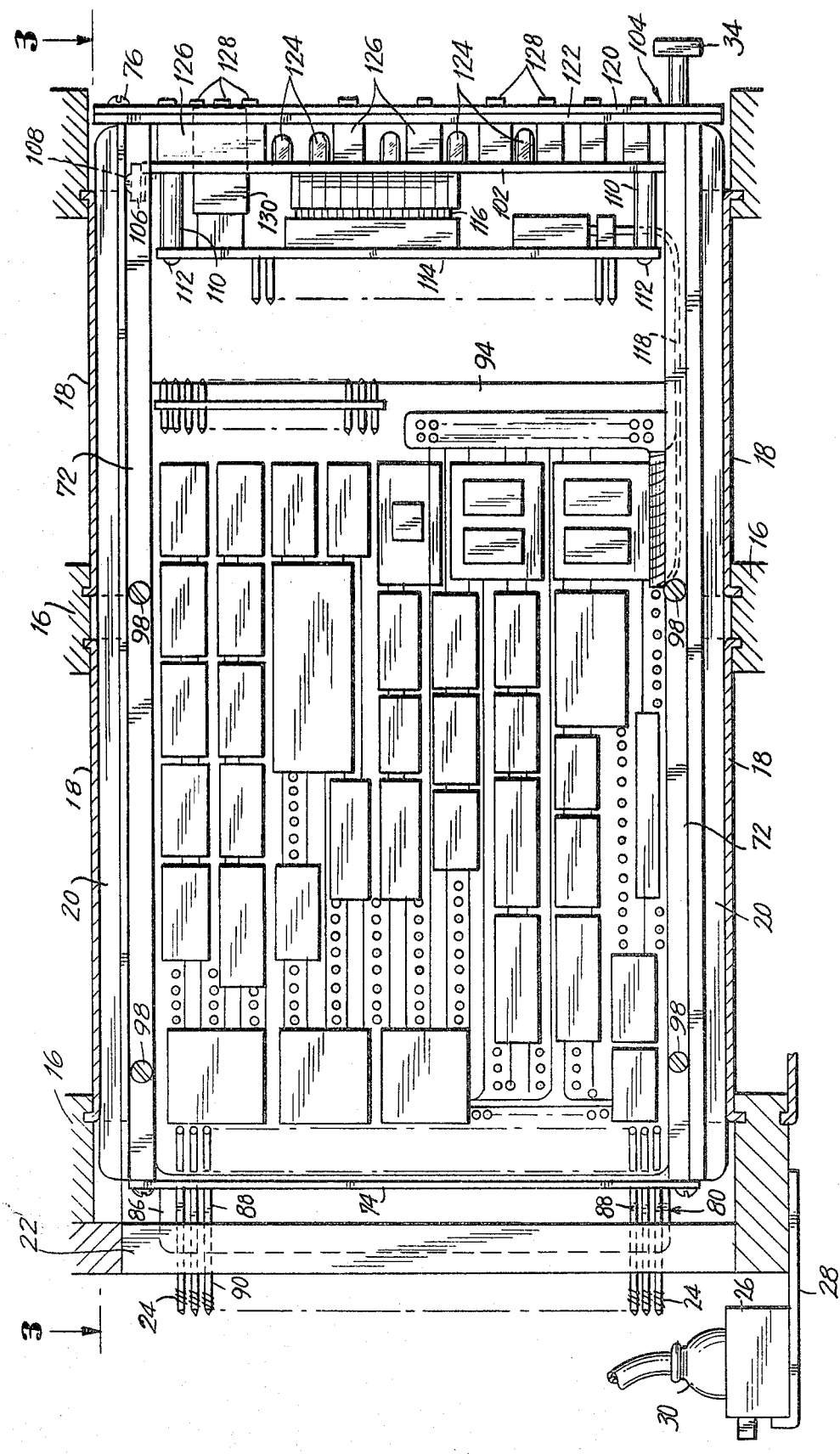
FIG. 2 is a fragmentary enlarged sectional view taken along 2—2 of FIG. 1 showing a side elevational view of the temperature module.
Figure 4:
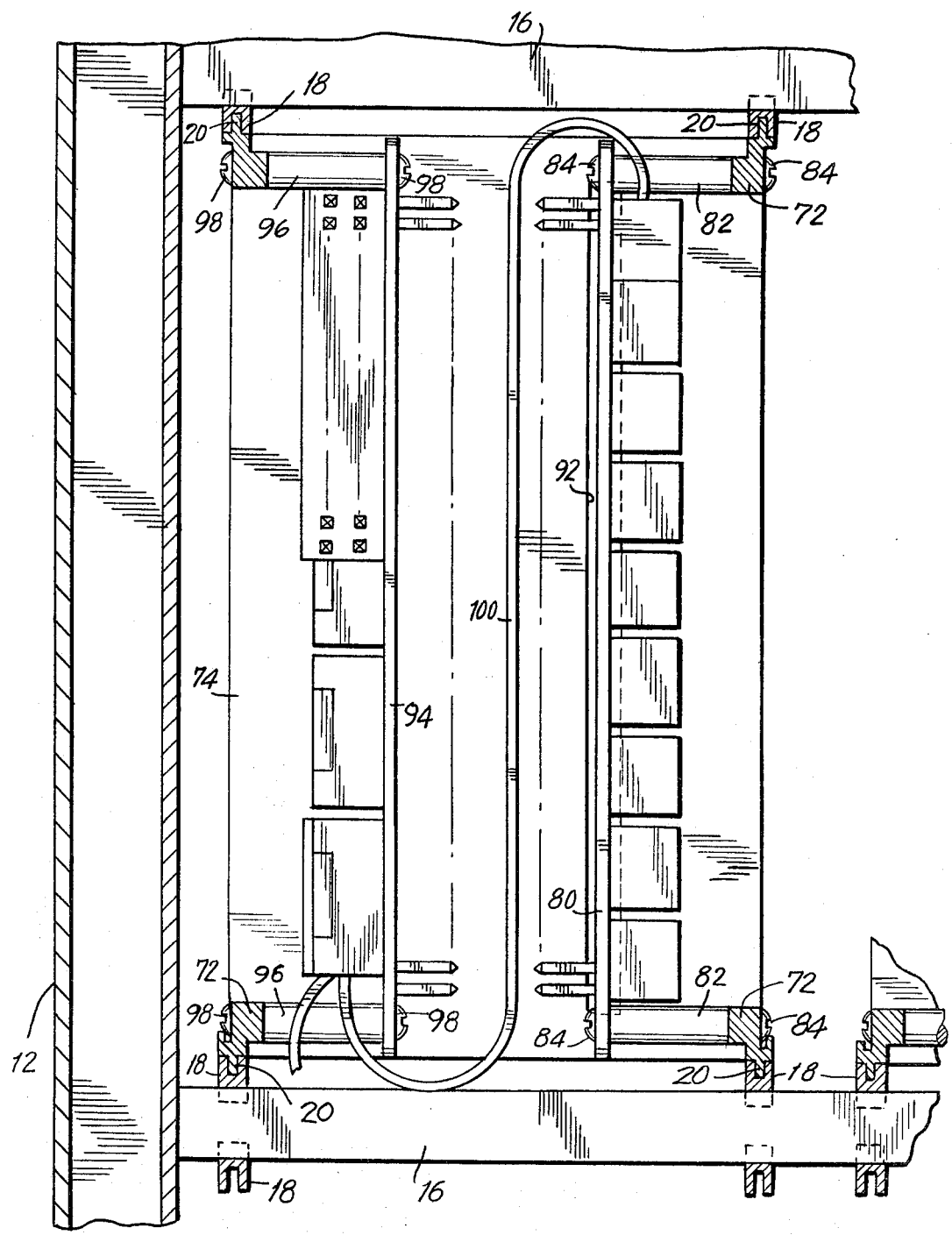
FIG. 4 is a sectional view taken along lines 4—4 of FIG. 3.

Each of the function modules 44, 46, 48, 50, 52, 54 and 56 includes four circuit boards as exemplified by the temperature module 44 illustrated in FIGS. 2-4. Specifically, each such module includes an I/O board 80 supported by means of spacers 82 and screws 84 to the corner supports 72 on one side of the module. I/O board 80 extends longitudinally of the module (from front to back) and is formed with a rearwardly projecting plug portion 86 in the rear thereof. Plug portion 86 is formed with an array of printed lead portions 88 on each side thereof, in this embodiment 50 lead portions on each side in opposed pairs for coupling with the corresponding one hundred channels of conductive array 24. Each socket 22 is provided with two parallel spaced rows of conductors 90 providing electrical connection with the corresponding printed leads 88 to provide electrical connection between the conductive array and the module. Rear wall 74 of the frame of each module is provided with an opening 92 to permit the passage of plug portion 88 of I/O board 80 therethrough. Also extending longitudinally of each function module is a microprocessor board 94 mounted on the other set of corner supports 72 by means of spacers 96 and screws 98. Microprocessor board 94 is electrically coupled to I/O board 92 by means of a multi-lead flexible ribbon cable 100. As best seen in FIG. 2, the third board, switch and LED board 102, extends transversely of the module and is positioned immediately behind front panel 104. Board 102 is mounted to a cross-bracket 106 by means of screws 108. Secured to the rear of switch and LED board 102, by means of spacers 110 and screws 112, is a display board 114. Display board 114 also extends transversely to the module and substantially parallel to the front panel 104. Display board 114 is electrically coupled to switch and LED board 102 by means of a multi-lead ribbon cable 116 while multi-lead flexible ribbon 118 couples microprocessor board 94 and display board 114.

The front panel 104 of each function module is formed with an outer indicia-bearing plate 120 and an inner switch and LED matrix plate 122, although a unitary plate having the indicia marked thereon could also be utilized. Switch and LED board 102 supports a plurality of LEDs 124 in registration with round openings in front panel 104 (see FIG. 5 by way of example) which permit the LEDs to be visible when actuated. The switch and LED board 102 also supports a plurality of switches 126 having actuator buttons 128 projecting through small rectangular openings in front panel 104. Switches 126 are manually operable for the selective setting of set points and the control of the respective modules, as more particularly described below.

Display board 114 supports a display module 130 which projects through a rectangular opening in switch and LED board 102 and in front panel 104 to provide a visual numeric readout. In one embodiment, display module 130 may be a four digit, seven-bar LED display of conventional design.

Figure 11:
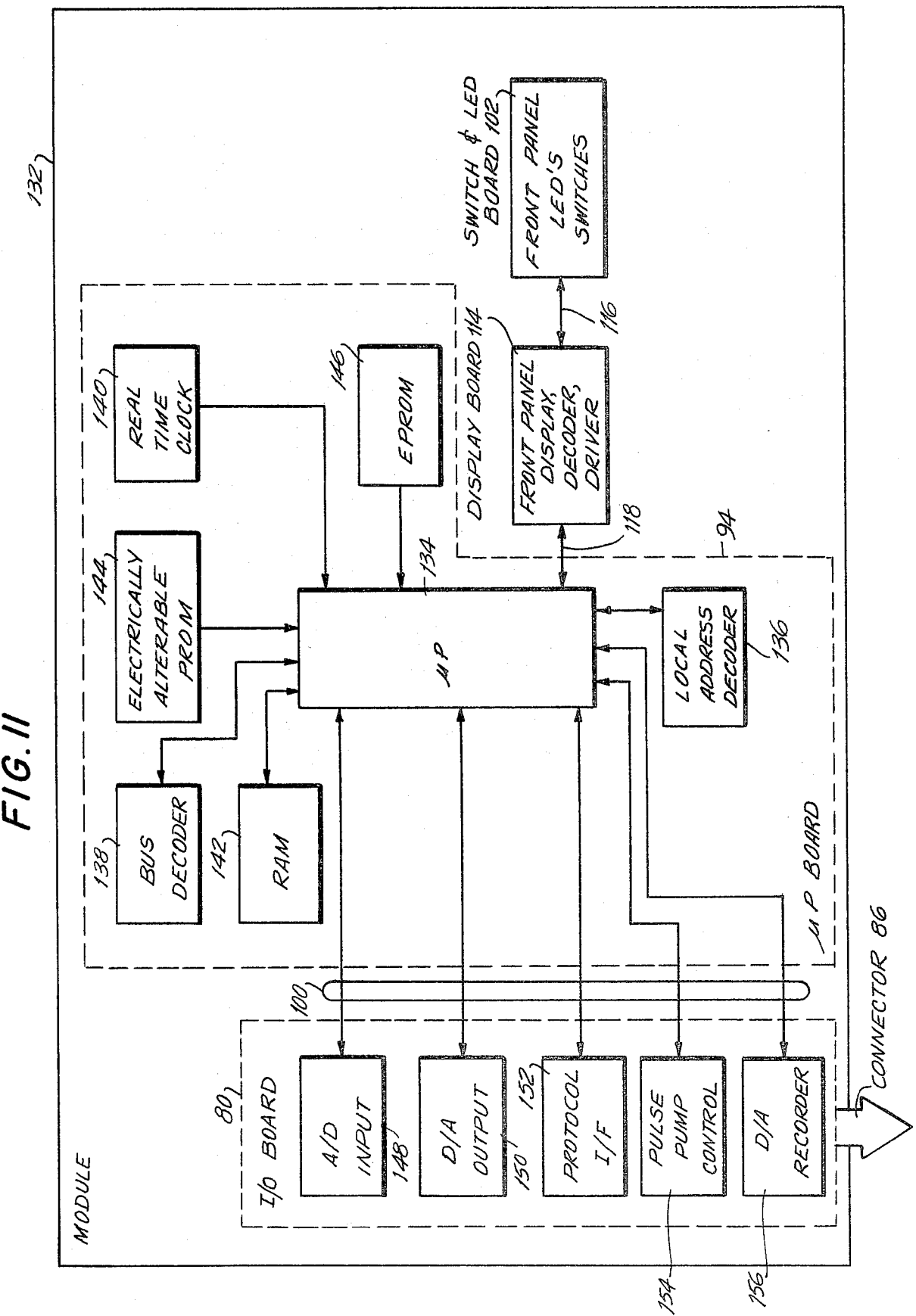
FIG. 11 is a block diagram of a typical function module in accordance with the invention.

Turning now to FIG. 11, the operation of a generalized function module 132 will be described. As discussed above, switch and LED board 102 supports front panel switches and LEDs and is coupled by cable 116 to display board 114 which supports a front panel display module 130 and associated decoder and driver circuits. Further, display board 114 transmits switch actuation signals to the microprocessor board 94 from switch and LED board 102 and transmits LED actuation signals to board 102 from the microprocessor board. The transmission function may be through a decoder if desired.

Display board 114 is coupled to microprocessor board 94 by cable 118. The heart of microprocessor board 94 is microprocessor 134 which may be, in one embodiment, a Motorola Model 6802. Also carried on microprocessor board 94 is a local address decoder 136, a bus decoder 138, a real-time clock 140 and memory means consisting of a RAM 142, an electrically alterable PROM 144 and an EPROM 146. The real-time clock is utilized for profiling functions. As used herein, the term "profiling" refers to the provision of a series of process time related or event related set points for each function at which it is desired that the process be at each point in time of the biochemical process being controlled and monitored.

Real-time clock 140 can be set and read as will be more particularly described below. Bus decoder 138 controls access to the common data line of the microprocessor board to control access to and from the microprocessor at the direction of the microprocessor. RAM 142 provides scratchpad memory to the microprocessor. RAM 142 is a random access memory which is modifiable by the microprocessor. EPROM 146 is an electrically programmable read only memory which is electrically programmed at the factory or by the user but is not modifiable by means of the microprocessor. The contents of EPROM 146 for each function module differs from those of the other function modules and contains the specific controlled program associated with the control scheme which is characteristic to the variable being controlled by that function module. EPROM 146 is selected to be of a non-volatile form upon power failure, so that the contents of the EPROM are not lost upon the disconnection of the module or other power outage. Electrically alterable PROM 144 is also selected to be of the non-volatile type but the contents thereof is alterable by the microprocessor, either in response to manual inputs from switch and LED board 102, or in the alternative, in response to signals from the computer data bus as more particularly described below. Electrically alterable PROM 144 stores input/output parameter data which translates sensor signals into a code usable by the microprocessor, as well as set point data consisting of time and function value information. The input/output parameter information is stored in the electrically alterable PROM 144 since such data may differ for different sensors.

Microprocessor board 94 is coupled to I/O board 80 by means of multi-lead cable 100. I/O board 80 is adapted to couple to the conductor array 24 and has five forms of input and output devices. Sensor input is provided by A/D (analog to digital) input device 148. In one embodiment, eighteen channels of the conductive array are directed to sensor input. D/A (digital to analog) output device 150 is provided to transmit control signals to sensors. In one embodiment, twelve channels of the conductive array 24 are allocated to this function. In the instrument console 10 in accordance with the invention, analog sensing and analog control are utilized, thereby necessitating the use of analog to digital and digital to analog conversion, but the arrangement in accordance to the invention could be utilized in conjunction with direct digital controls and digital output sensors. Protocol I/F (interface) device 152 controls access to the computer bus, which both allows communication between modules as more particularly described below, and further permits communication between an external computer and the modules. Each module is assigned one time slot for access to the computer bus, the particular time slot being coded in EPROM 146. In one embodiment each time slot consists of 1/20th of a 20 millisecond cycle. Due to the slowness of the process and the frequency of operation of the respective modules, at worst, each module will encounter a busy computer bus once during a 20 millisecond cycle, a time duration which is of no consequence in the type of biochemical processes at question. This results from the fact that every module does not communicate every cycle. In one embodiment twenty-one channels are devoted to the computer bus. Each module is provided with a distinctive address code to facilitate communication.

I/O board 80 also includes a pulse pump control 154 which is utilized where the module drives a pump, as in the case of the pH and antifoam modules. The pumps 60, 62 and 64 are step motor-actuated pumps operated in response to controlled numbers of pulses representative of the quantity of liquid to be fed. Such pulse signals are applied on the associated channel assigned to pump control by pulse pump control 154. In one embodiment, twelve such pump control channels are assigned.

Finally, I/O board 80 includes a D/A (digital to analog recorder output 156 adapted to drive, on a selected channel, a recorder such as one channel of recorder 38. Recorder 38 is adapted to function on analog signals, and accordingly, the microprocessor transmits data in digital form which are converted to analog form in D/A recorder output 156 for transmission on the selected channel of conductive array 24 to recorder 38. In one embodiment, twelve channels are assigned to this recorder function in the conductive array 24. However, if additional control output channels are required, one or more of the recorder channels can be utilized for this purpose.

The representative module 132 of FIG. 11 is a standard module common to all of the function modules. In order to tailor the module to a particular purpose, only EPROM 146 and switch and LED board 102 need be selected, together with an appropriate indicia bearing plate 120 defining the front panel of the module. EPROM 146 is a plug-in component for this purpose, and as described above, switch and LED board 102 can be readily substituted due to the releasable mounting thereof and the plug-in nature of the coupling of the ribbon leads. Thus, should a particular module fail it is necessary merely to maintain a spare EPROM 146 and spare switch and LED boards to transfer any single spare module to the desired function. Such modification can be rapidly achieved so that a continuing process can generally be saved notwithstanding the failure of a particular module. Electrically alterable PROM 144 can be readily set, either manually or by an external computer. If the user has an apparatus for programming an EPROM, separate EPROMs for each function need not be maintained. The failure of one module does not halt the operation of the other modules.

Because each module is microprocessor controlled, various failure schemes can be programmed into the EPROM 146. Thus, if a dynamic failure scheme is followed, upon detection of a malfunction the microprocessor will be instructed to set the control to a prescribed number. In an alternative static failure scheme, if the module is functioning, but not properly, the microprocessor can be instructed to maintain the process variable at its current value. A third scheme, an interrupt failure scheme, would be used where safety is a factor, as in the case of the pressure control. In the interrupt scheme, upon the detection of a power failure, the microprocessor would transmit a control signal to the pertinent valve to open the valve to prevent damage to the equipment due to undesired pressure build-up. In any of these failure modes, the microprocessor can be programmed to store the process time of failure in the electrically alterable PROM 144 and can further be programmed to perform self-check programs periodically to detect malfunctions. Various malfunction alarm or process failure alarms can be operated by each module. Thus, by way of example, the LEDs or selected ones of the LEDs on switch and LED board 102 can be caused to blink. A light or buzzer alarm built into another module such as the power module 32 may be actuated. Finally, an external alarm such as a buzzer can be actuated by the transmission of an alarm signal along a selected output channel. Referring to FIG. 1, selector terminals of terminal block 66 and 68 can be connected to a particular channel on which an alarm signal will be applied and an alarm detecting device such as a buzzer may be coupled to the terminal of the terminal block.

It is apparent from the foregoing discussion that while each module is of essentially universal application, with the exception of the EPROM 146 and the switch and LED board 102, nonetheless, means must be provided for selectively coupling the I/O board 80 to selected channels assigned to that particular module. For this purpose, a group of switch devices 158A, 158B, 158C and 158D is mounted at the output of board 80 (see FIG. 2A). Each of said switch devices includes a plurality of manually setable switches which determine which channels are coupled to the circuitry of I/O board 80. Thus, by way of example, switch device 158A is provided with twelve switches and may be utilized to coupled D/A output device 150 to the one or two selected channels which are to receive control signals. Similarly, switch device 158B is provided with eighteen switches for selectively coupling the one or more sensor inputs which are to be applied to A/D input device 148. Switch device 158C is provided with twelve switches 160 for controlling the one or more recorder channels to which the D/A recorder device 156 of the module is to be connected. Finally, switch device 158D is provided with twelve switches 160 for the selection of the one or more pump channels to which pulse pump control 54 is to be connected.

Referring now to FIGS. 9 and 10, the sensor module 65 will be described. The front panel 161 of the sensor module bears set-screws 162 and 164 for the calibration of the speed module. Immediately below the speed calibration screws, are three screws 166, 168 and 170 used for the calibration of the dissolved oxygen module. In addition, two pairs of plug-in sockets 172 and 174 are provided for respectively receiving either galvanic or polarographic type dissolved oxygen probes. Immediately below are set-screws 176 and 178 for calibrating the temperature module while immediately therebelow are set-screws 180 and 182 for calibrating the pH module. Connector 184 is for receipt of the cable from the pH probe. Module 65 is constructed in the same manner as the function modules, being defined by corner support 72 and guided by ribs 20 projecting therefrom. Two circuit boards 186 and 188 are mounted within the module and carry the signal conditioning circuitry required to condition certain sensor input signals into a form usable by the modules, and further required to condition certain ciontrol output signals before transmission to the controlled devices. Circuit board 188 is supported in a bracket 190 mounted on bottom plate 192, which is in turn supported between the bottom corner supports 72. Circuit board 186 is supported by spacers 194 and screws 196 in the manner discussed above in connection with I/O board 80. Like I/O board 80, circuit board 186 is provided with a plug portion 198 for receipt in a socket 22 supporting conductors 90 coupled to conductive array 24 as discussed above. In this manner, the sensor module is coupled to the desired channels of the conductive array 24. Switching devices (not shown) may be provided to permit manual selection of channels in coordination with the channel selection of the respective modules. The rear wall 74' of the sensor module bears temperature input socket 200 for connection to a temperature sensor and temperature output socket 202 for connection to a temperature control device. Further, the module includes a speed-in socket 204 for connection to an agitation speed sensor and speed control socket 206 for connection to a agitation speed control mechanism. Finally, in this embodiment of the sensor module, plug 208 is provided for coupling to the antifoam sensor. The operation of the various probe calibrations and control devices will be described more particularly in connection with the discussion of each function module.

Figure 12:
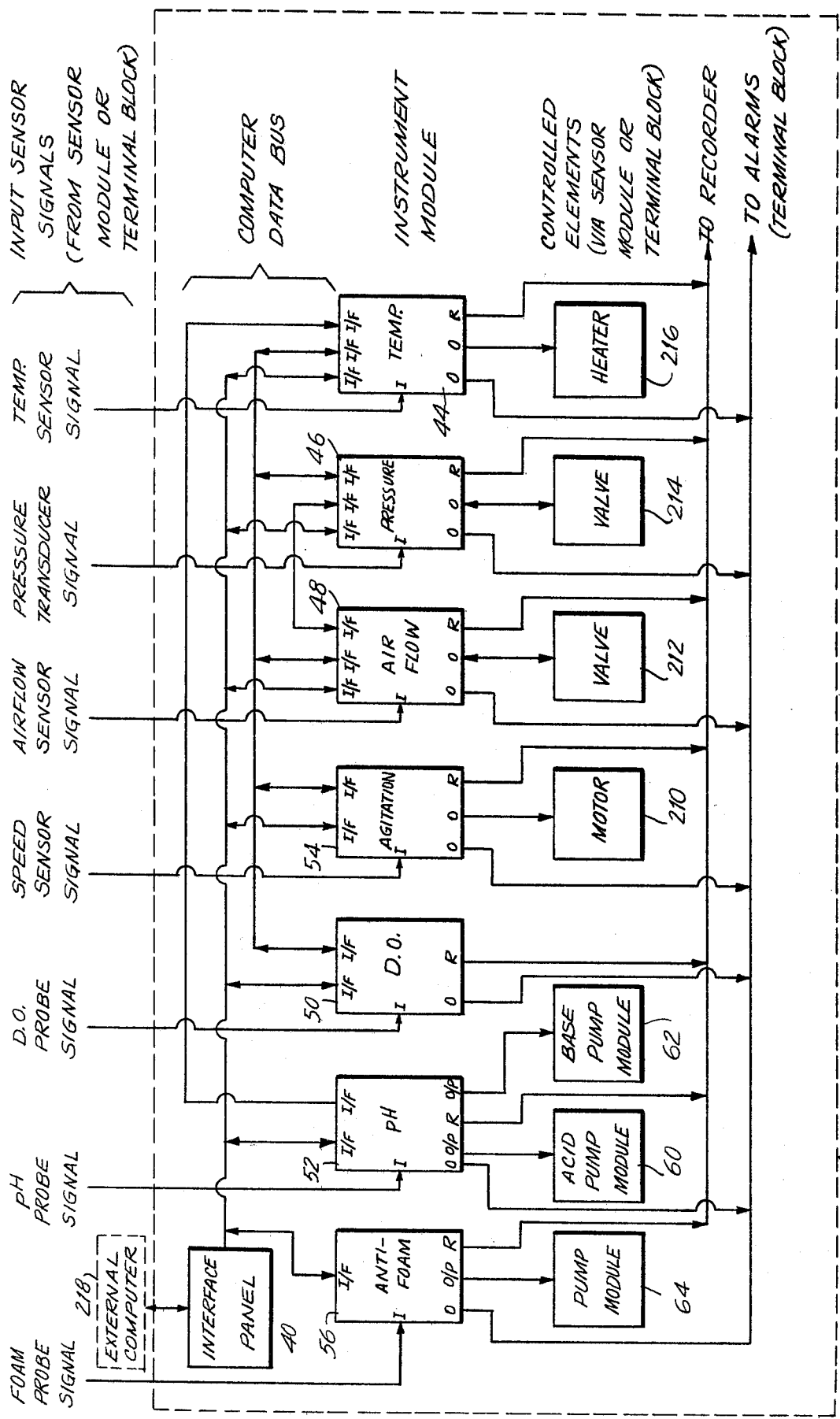
FIG. 12 is a block diagram of the instrument console in accordance with the invention.

Referring now to FIG. 12, the coordinate operation of the console in accordance with the invention will be more particularly described, like reference numbers being applied to like elements heretofore described. Antifoam module 56 monitors the signal of a foam probe as conditioned in the sensor module, and in response thereto (the detection of foam), actuates pump module 64 to dispense measured amounts of antifoam material, as determined by the program stored in the memory associated with the microprocessor. Various strategies for the feeding of antifoam material may be followed. The microprocessor incorporated in antifoam module 56 is sufficiently flexible to follow any desired programmed approach for the feeding of antifoam material. In this block diagram, "R" represents a recorder output which may be connected, "O" is one of the D/A output device 150 outputs coupled to an alarm as at one of terminal blocks 66 or 68 or internal to the console 10, for the purpose of annunciating an antifoam module failure or process failure. "O/P" represents an output on one channel associated with D/A output device 150 for actuation of the pump or a solenoid and an output on one channel associated with pulse pump control device 154 for the incremental feeding of the antifoam material in response to the pulsing of the step motor of pump module 64. The foam probe signal is applied at an input "I" representative of one of the sensor input channels associated with A/D input device 148.

In like manner, pH module 52 operates in response to a pH probe signal to operate one of the acid or base pump modules 60, 62, to operate a recorder and to sound alarms, if desired. pH module 52 is shown joined to temperature module 44 through the computer data bus as indicated by "I/F" representative of the protocol I/F device 152. This optional coupling permits control of temperature and pH in an interactive manner in addition to control of pH and temperature in response to the respective pH and temperature sensors, the respective temperature and pH data being transmitted to the pH and temperature modules through the computer data bus. If desired, other inter-module coupling can be made through the computer data bus whereby the operation of any function module can be governed by the data collected by another function module or any function module can control the set point of another function module if the priorities of the control strategy so dictate. This intercoupling of the modules also permits programming the microprocessor in accordance with an event based set point profile. An event based set point profile permits a function module to control its function to a set point value when another function reaches a predetermined level. For example, pH module 52 can be programmed to control the pH to a predetermined level when temperature reaches a predetermined value. Such event based set points are generally empirically determined.

Dissolved oxygen module 50 receives its input from a dissolved oxygen probe signal received from the sensor module and can actuate a recorder or alarms. However, dissolved oxygen is controlled by control of agitation, air flow and pressure in accordance with a scheme selected by the operator, and for this purpose, the dissolved oxygen module is coupled to the agitation module 48, air flow module 54 and pressure module 46 through the computer data bus, the dissolved oxygen module serving to establish set points in the respective agitation, air flow and pressure modules in accordance with preestablished priority schemes for the purpose of controlling dissolved oxygen. The dissolved oxygen module is also coupled to the temperature module 44 to receive temperature data therefrom for use in determining the proper control steps required to effect maintenance of dissolved oxygen at the desired set points during the process. As in the case of all of the other modules, the set points are stored in memory, the control strategy is stored in memory and the module is operated by the internal microprocessor of the module.

Agitation module 48 receives a speed sensor signal and operates agitator motor 210 coupled to one of the output channels associated with D/A output device 150. As in the case of all of the modules, recorder and alarm outputs may be provided.

Air flow module 59 receives an air flow sensor signal from a flow sensor coupled to the sparger. While the module is identified as an air flow module, it could be used to control any gas fed to the biochemical process. Air flow module 59 controls a flow control valve 212 in response to a control signal transmitted by the D/A output device 150 of the air flow module. Further, the air flow module 54 and the pressure module 46 are coupled through the computer data bus since air flow and pressure are interrelated and the scheme for the respective control thereof would be dependent on detecting the measured value of both air flow and pressure. Pressure module 46 receives a pressure transducer signal and controls valve 214 which is generally a vent valve in the vessel in which the process is being conducted. Finally, temperature module 44 operates in response to a temperature sensor signal and serves to control a heater 260. It is apparent that cooling devices could likewise be controlled by the temperature module and that temperature could be controlled by sensing and controlling the temperature of fed materials such as nutrients within the scope of the invention.

Interface panel 40 is depicted in FIG. 12 interconnected to each of the function modules to the computer data bus. An external computer 218 may be coupled to the interface panel either for the purpose of actually performing process control through operation of the respective modules, or for the purpose of logging data from the modules, or for the purpose of setting set points in the modules, the microprocessor in each module then performing the control function in accordance with its pre-programmed strategy.

Figure 13:
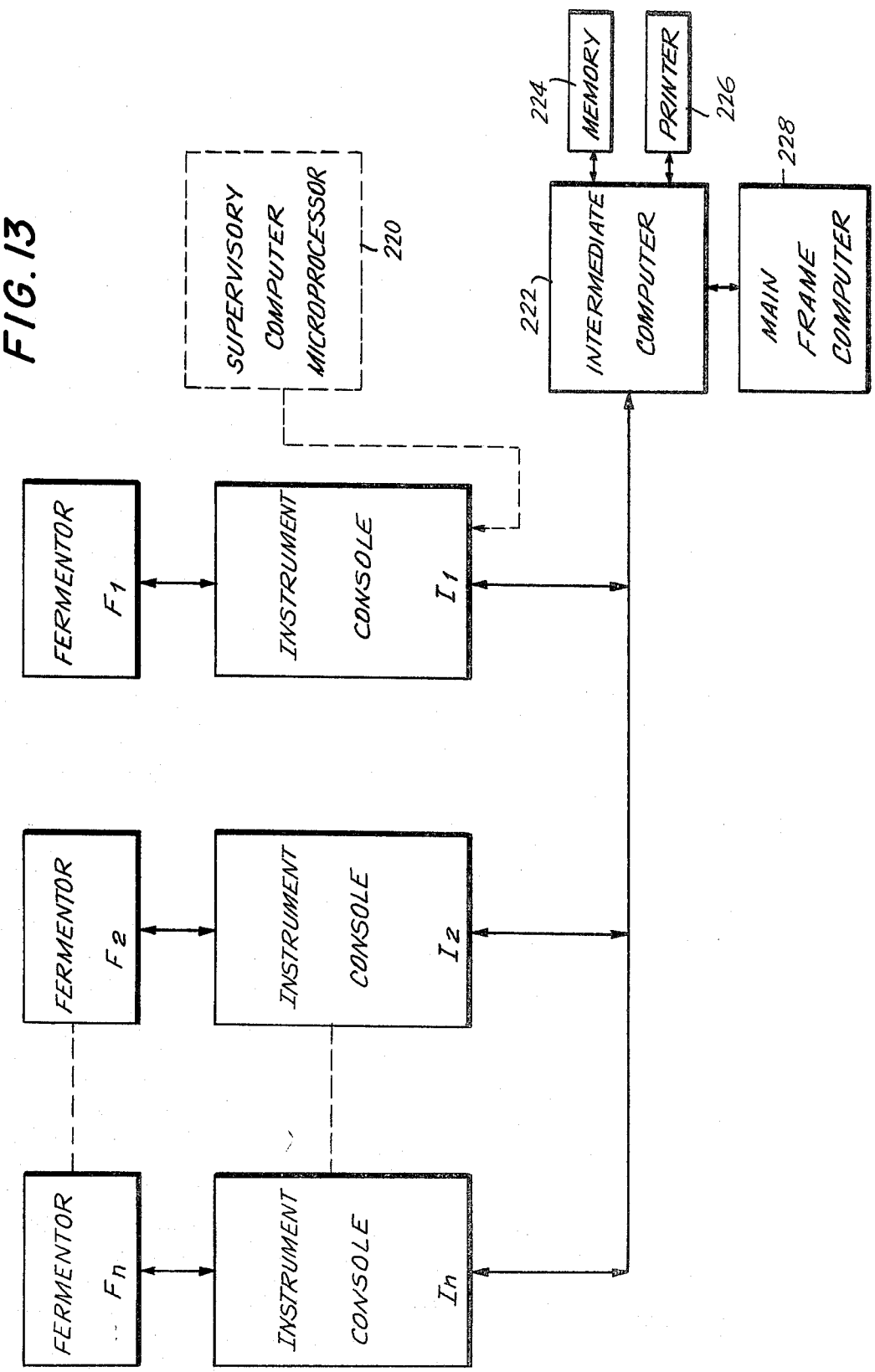
FIG. 13 is a block diagram of a multi-fermentor system incorporating instrument consoles in accordance with the invention.

A multi-fermentor system is depicted in FIG. 13, each fermentor $F_1$, $F_2$,–, $F_n$ having an associated instrument console (corresponding to instrument console 10) $I_1$, $I_2$,–$I_n$. Each instrument console may be connected to a supervisory computer (microprocessor) for the separate control thereof as described in connection with FIG. 12. In the alternative, all of the instrument consoles can be commonly coupled to an intermediate computer 222 having associated memory 224, printer 226 and other peripheral devices. Intermediate computer 222 can, on a multiplexed time-sharing basis log data, compute the changes, monitor values and input profile data to the instrument consoles and can perform the process control as described in U.S. Pat. No. 3,926,737 discussed above. Main frame computer 228 may be used for fermentation optimization, design of overall fermentation system computer control strategy and correlation on an off-line or other than real-time basis.

Figure 5:
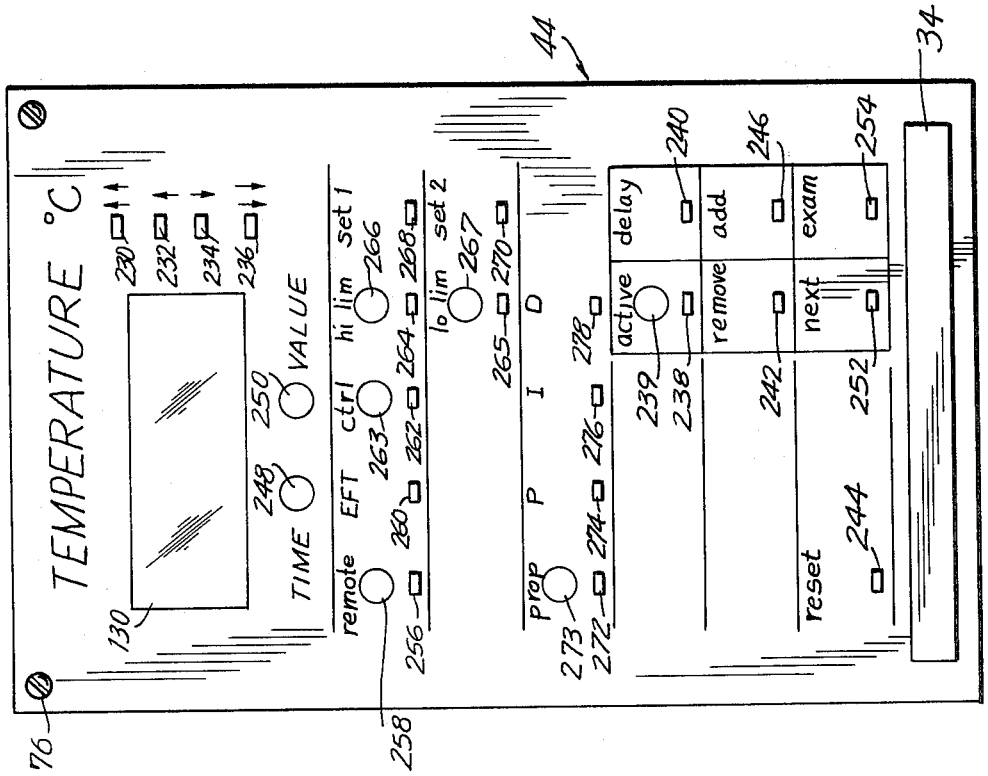
FIG. 5 is a view of the front panel of the temperature module in accordance with the invention.

Referring now to FIG. 5, wherein the front panel of the temperature module 44 is depicted, the operation of the manual input means in accordance with the invention as it applies to the temperature module will be described. The front panel of the temperature module is provided with an alpha-numeric display 130, a plurality of LED indicia represented by circles and a plurality of switches represented by small rectangles. To the right of display 130 are four vertically spaced switches 230, 232, 234 and 236 which are used to displace the numeric value displayed in the display for setting purposes. Switch 232 advances the displayed value at a slow rate while switch 230 advances the displayed value at a rapid rate. Switch 234 decreases the displayed value at a slow rate while switch 236 decreases the displayed value at a rapid rate.

Where switches are utilized for the purpose of setting values, a switch operating protocol has been programmed into the microprocessor. The first actuation of the switch, as by pushing the button thereof once, activates the setting function and displays the then current value in display 130. The displayed value may be altered by means of switches 230, 232, 234 and 236 in either direction, either rapidly or slowly. If the switch is reactuated within a prescribed time period, by way of example, five seconds, then the setting will return to the original setting. If after alteration the actuating switch is not reactuated within the prescribed period, then after the passage of the prescribed period of time the value is set to the value displayed in the display. If no entry is made by way of switches 230, 232, 234 or 236, after the passage of the prescribed period of time, the display returns to the current value of the function being monitored. Said current monitored value is the default condition for each of the modules in the absence of instruction by input or otherwise, except for antifoam module 56, as described below.

As discussed above, set point profiling may be established for each of the functions to be controlled, including, by way of example, temperature. A set point profile is the ordered list of the elapsed fermentation times and set point values to be initiated without operator intervention. Generally, a time related profile consists of sets of two variables, a time and an associated value. As described above, the profile may be stored in the electronically alterable PROM 144 by an external computer. However, if the profile is to be manually entered, or if the user wishes to modify or merely examine an existing stored profile, "active" switch 238 is actuated, causing LED 239 to be actuated providing a visual indication of profiling operation and the microprocessor disposed in a mode to display and/or modify the profile.

"Delay" switch 240 permits the operator to delay the profile by a fixed plus or minus timing increment. A positive delay time retards the profile, while a negative time accelerates the profile. Applying the switch protocol, when the delay switch 240 is actuated, display 130 would show "O". Thereafter, within the five second allowed time frame, the displayed value can be increased or decreased by means of switches 230, 232, 234 and 236 to select the desired positive or negative delay. If the operator changes his mind or is not satisfied with the setting, by actuating delay switch 240 within the five second time frame, the delay is not entered. If no further action is taken for five seconds, then the set delay is incorporated into the profile stored in electrically alterable PROM 144.

"Remove" switch 242 is used to remove set points. When remove switch 242 is actuated, the operator may, using switches 230, 232, 234 and 236, set the display to a desired time representative of the set points to be removed. If the remove switch 242 is not reactuated within the five second period, then the set point at the displayed time is removed. In order to clear the entire set point profile with one command, the operator simply actuates remove switch 242 and, instead of entering any values, actuates "reset" switch 244. In order to avoid accidental elimination of the profile, a multiple actuation of resetting switch 244 is required. In one embodiment, four such actuations with no predetermined time period gaps therebetween is required to clear an entire profile. "Add" switch 246 is used to add set points to the profile. When the "add" switch 246 is actuated, the display is cleared and "TIME" LED 248 is actuated to indicate display of a time. The operator then advances the displayed time indication by means of switches 230, 232, 234 and 236 until the desired elapsed process time is reached. The "add" switch is actuated again, setting the time into the profile and causing "VALUE" LED 250 to light ("TIME" LED 248 being extinguished). The display is again cleared and the desired temperature value is set by means of switches 230, 232, 234 and 236. If "add" switch 246 is actuated within the predetermined time, then the new set point is not entered. If nothing is done within the prescribed period of time after entry of the temperature value into the display, then the desired set point is entered into electrically alterable PROM 144 and the display returns to display of actual monitored temperature value.

When "next" switch 252 is actuated, the time and value of the next set point change within the stored profile is displayed. First the time value is displayed, with "TIME" LED 248 lit, and then, in automatic sequence, the value at that time is displayed with "VALUE" LED 250 lit. The display automatically returns to measured value of temperature as determined by the sensor.

When "exam" switch 254 is actuated, the display starts at 0 and automatically sequentially displays the set point values in the entire profile alternately displaying time and value, with the "TIME" and "VALUE" LEDs 248 and 250 being alternately lit. By means of switches 230, 232, 234 and 236, specific points in the profile can be reached and examined, if desired. The precise time of a set point to be removed can be determined by this process.

When "remote" switch 256 is actuated, the module is adapted for remote computer programming or control. This state is indicated by a lit "remote" LED 258. When "EFT" (elapsed fermentor time) switch 260 is actuated, the elapsed process time of the process being controlled is displayed. If, in this setting, the displayed value is altered by means of switches 230, 232, 234 or 236, the elapsed process time as seen by the microprocessor can be altered at will. "ctrl" (control) switch 262, when actuated, places the module in a "control" mode, wherein the temperature of the process is controlled automatically by the microprocessor. Processor alarms may be set by means of "hi lim" switch 264 and "lo lim" switch 265. These switches operate in accordance with the switch protocol, and when one is depressed, the high limit and low limit values for the alarm may be set by means of switches 230, 232, 234 and 236. An excursion of temperature beyond the high limit is indicated at least by the lighting of "hi lim" LED 266 while an excursion of temperature below the set low limit lights "lo lim" LED 267. Audible alarm outputs may be provided as discussed above. LEDs 266 and 267 may flash if desired to render them more visible. To provide for no alarms, the high alarm is set to the maximum upper limit and the low alarm is set to the minimum or zero limit.

The modules in accordance with the invention are capable of two types of control, on/off control and "PID" (proportional/integral/derivative) control. While theoretically, both types of control require control action upon a deviation from the set point, as a practical matter, such an approach would lead to constant control which is neither desirable nor practical. In order to avoid continuous control with the attendant constant operation of control relays, each set point has associated therewith, a dead band, a band within which deviation from the set point will not effect control. While the dead band is adjustable, adjustment to zero is not generally permitted. When "set 1" switch 268 is actuated, the current set point is displayed. The current set point can be altered by means of switches 230, 232, 234 and 236. When "set 2" switch 270 is actuated, and a value set by means of switches 230, 232, 234 and 236, then a current set point consisting of the band between the value of "set 1" and the value of "set 2" becomes the current set point. On the other hand, if "set 2" switch 270 is actuated twice within the predetermined time period, without an intervening adjustment, then the number set in the display becomes a ±dead band. Thus, for example, if the value "5" is set after actuation of "set 2" switch 270 twice, a dead band of ±5° is established, which dead band will apply not only to the current set point but to all future set points in the profile. While it is noted that, in the embodiment depicted, a different dead band cannot be set for each profile value, the apparatus in accordance with the invention could be programmed to permit such a setting, in which case each profile would consist of three entries, time, value and dead band.

Turning now to PID control, when "prop" switch 272 is actuated, "prop" LED 273 is lit and the control mode is PID. If "prop" switch 272 is not actuated, then the module is operating in an on/off mode. "Proportional control" refers to control proportional to the degree of deviation from the set point, in other words, the further the deviation from the set point the greater the correction. "Integral control" relates to the time the variable under control has deviated from its set point, in other words, the longer the deviation has persisted, the greater the correction. "Derivative control" relates to the rate at which deviation from the set point occurs, in other words, the faster the rate of deviation from the set point, the greater the correction. As in on/off control, the deviation is measured from a dead band. When "P" switch 274 is actuated, the number set in the display by means of switches 230, 232, 234 and 236 represents the difference between the set point and the measured value at which maximum corrective action is effected, in other words, at which maximum heating or cooling increase is effected, hereinafter referred to as "maximum control." An algorithm programmed into the microprocessor memory controls the amount of corrective action applied, between no value deviation and the set maximum. Generally, the control action is not linear, a logarithmic relation being a common approach. Similarly, "I" switch 276 and "D" switch 278 may be actuated to set the maximum deviation in time of deviation or rate of deviation, respectively, which causes maximum control. If the "P", "I" or "D" setting is zero, then that function is inoperative. Generally, the "proportional" and "integral" or the "proportional" and "derivative" control approaches are used in conjunction. Or, if desired, all three control approaches can be used in conjunction.

The foregoing description directed to temperature module 44 is equally applicable to pressure module 46, agitation module 48 and air flow module 54, which are identical in structure and operation (but not in the programming of the EPROM 146 or the program input of the electrically alterable PROM 144). Substitution of these modules in case of breakdown merely requires the reprogramming or replacement of EPROM 146 and the reprogramming of electrically alterable PROM 144, without any change to switch and LED board 102 aside from a cautionary exterior label. Dissolved oxygen module 50, pH module 52 and antifoam module 56 all incorporate the LEDs and switches of the temperature module 44 and like reference numerals have been applied to the views of the front panels of these modules in FIGS. 6–8.

Figure 6:
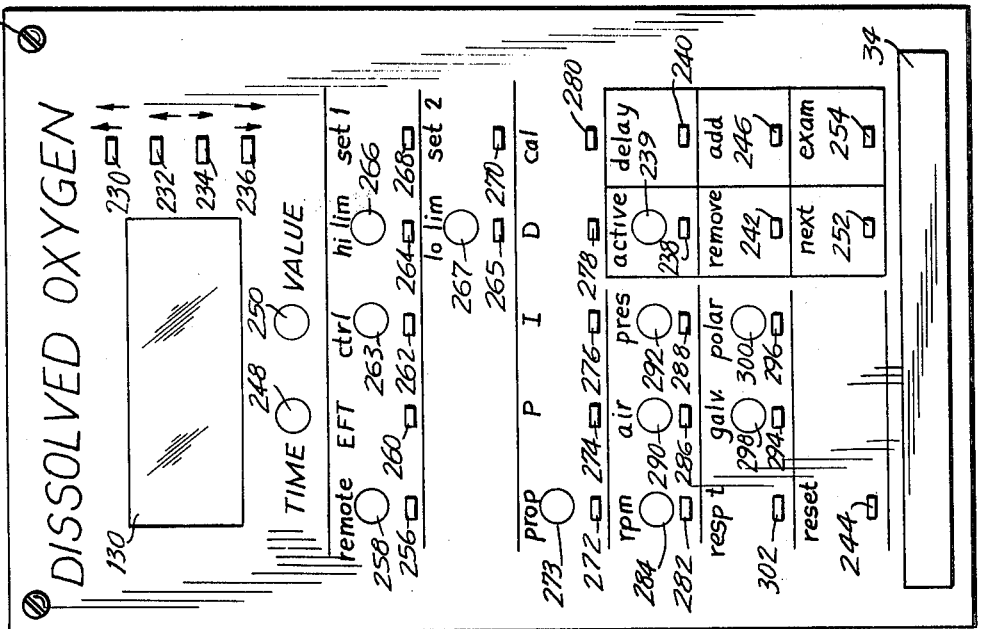
FIG. 6 is a view of the front panel of the dissolved oxygen module in accordance with the invention.

Referring to FIG. 6, the front panel of the dissolved oxygen module 50 includes a "cal" switch 280 which when actuated prepares the module for calibration. Calibration is accomplished by placing the dissolved oxygen probe in a standard known liquid and adjusting the displayed value by means of switches 230, 232, 234 and 236 to the known calibrated value. When the "cal" switch 280 is activated again, the module is calibrated to a particular probe. For electrical calibration, the "cal" switch 280 is actuated with the probe disconnected and set screws 166, 168 and 170 are adjusted until the display reads zero. The "cal" switch is actuated again and the dissolved oxygen module is ready for use. When "rpm" switch 282 is actuated, "rpm" LED 284 is lit and display 130 displays the monitored speed value as transmitted over the computer data bus from agitation module 48. By manipulation of switches 230, 232, 234 and 236, agitation speed can be controlled from the dissolved oxygen module. In effect the set point for agitation speed is reset by communication from the dissolved oxygen module over the computer data bus to the agitation module, the program of the agitation module giving priority to the instructions from the dissolved oxygen module. In like manner, "air" switch 286 and "press" switch 288 perform like functions with regard to air flow rate and pressure in conjunction with the air flow module 54 and pressure module 46. Further, "air" LED 290 and "press" LED 292 provide a visual indication of the actuation of the respective switches 286 and 288.

As discussed above, the dissolved oxygen module is adapted for use with either a galvanic or a polarographic probe, and accordingly, "galv" switch 294 and "polar" switch 296 are utilized to set the dissolved oxygen module to cooperate with the actual form of probe being utilized. "Galv" LED 298 and "polar" LED 300 are provided to give a visual indication of the actuation of the respective switches 294 and 296. Finally, "resp t" (response time) switch 302 is used to set the response time of the dissolved oxygen module in accordance with the response time of the dissolved oxygen probe. Dissolved oxygen probes do not give instantaneous readings and accordingly, it is necessary to set a response delay, usually on the order of 40 seconds. By actuating switch 302, and by setting the delay by means of switches 230, 232, 234 and 236, the desired response time delay may be set. As noted above, in other respects, the dissolved oxygen module functions in the same manner as temperature module 44 in terms of input and display.

Referring now to FIG. 7, pH module 52 includes the switches and LEDs of the temperature module 44 and further includes "cal" switch 280 discussed above in connection with the dissolved oxygen module. The calibration of pH is achieved by actuating "cal" switch 280, placing the pH probe in a liquid of a known pH of, for example, 7, and turning set screws 180 and 182 on sensor module 160 until the display reads "7". Thereafter, the "cal" switch is actuated once to release the display and again to reset for calibration and the pH probe is put in a liquid of a known pH, for example, of a pH of "8". By means of switches 230, 232, 234 and 236 the displayed value is set at the known value, thereby effecting calibration, at which point the "cal" switch 280 is again actuated to release the calibration mode.

When "mix t" switch 304 of pH module 52 is actuated, the duration of the interval between cycles of acid or base addition may be set by manipulation of switches 230, 232, 234 and 236. In like manner, when "add t" switch 306 is actuated, the duration of each cycle of addition of acid or base may be set. Switches 304 and 306 are provided where it is desired to add the acid and base in controlled cycles to ensure that the reaction of the process to each increment of acid or base is detected before the next increment is applied.

Frequently, it is desirable to add acid or base manually to the process and it is frequently desirable to know the total of acid and base added to the present time. For this purpose, "acid" switch 308 and "base" switch 310 are provided for setting the module to respond with regard to acid or base, with "acid" LED 312 and "base" LED 314 providing a visual indication of the status of the module. When so set, actuation of "total" switch 316 causes the display of the total acid or base dispensed thus far in the process, depending on which of switches 308 or 310 is actuated. Similarly, the actuation of "man" switch 318 causes the manual dispensing of either acid or base, depending on which of switches 308 or 310 is actuated, for a duration so long as switch 318 is actuated. "Man" LED 320 is provided to visually indicate the actuation of switch 318. The remaining switches and LEDs function in the like manner as those discussed above.

Referring now to FIG. 8, the switches and LEDs of antifoam module 56 correspond to temperature module 44 except that the set point represents a programmed rate of antifoam material feed and the default display is the total of antifoam material added up to the current point in the process. In this case, actuation of "cal" switch 280 causes antifoam pump 64 to pump a predetermined amount of antifoam material which is pumped into a graduated measuring cylinder, the measured quantity then being entered by means of switches 230, 232, 234 and 236 into the display to effect calibration. A second actuation of "cal" switch 280 releases the antifoam module 56 from the calibration mode. Actuation of "man" switch 318 causes manual feeding of the antifoam material for so long as the switch is actuated, "man" LED 320 providing a visual indication of such manual operation. In addition to use of antifoam materials, foam is also broken up in fermentation processes by mechanical foam breaking apparatus. The actuation of "mech" switch 322 actuates such mechanical apparatus, such actuation being indicated by "mech" LED 324. It should be noted that antifoam pump module 64, as well as acid pump module 60 and base pump module 62 are perstaltic pumps and are located at the lowest level of the console to avoid damage to other modules should a leak develop. However, other forms of liquid feed devices may also be utilized, such as selenoid actuated feed devices.

As referred to above, an event based set point profile may also be used. In this embodiment, "active" switch 238 is actuated to enable the microprocessor to receive set point data. When "add" switch 246 is actuated and the "time" entry set to zero as described above, the microprocessor program determines that an event based set point is to be set and causes the display 130 to display in sequence, in response to a sequential operation of "next" switch 252, a series of symbols representative of "equals", "less than", "greater than", "less than or equal to" and "greater than or equal to". When the desired symbol is displayed and "add" switch 246 actuated again, a series of symbols representative of the variable the value of which is to trigger control are sequentially displayed in response to actuations of "next" switch 252. When the desired symbol is displayed and "add" switch 246 actuated again, the display is disposed to receive a value by means of switches 230, 232, 234 and 236. A last actuation of "add" switch 246 sets the event based set point in memory. In this embodiment, when an event based set point is reached, it controls the operation of the function thereafter until the next event based set point is reached.

As noted above, other forms of modules and other control functions can be readily incorporated in the function modules in accordance with the invention by reason of the flexibility thereof provided by the separate microprocessor associated with each module. It should also be understood that other methods of mounting the respective modules and other approaches for packaging the respective modules may be adopted within the scope of the invention.

It will thus been seen that the objects set forth above, and those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A module for monitoring and control of one of a plurality of variables in a biochemical process in response to sensor output signals comprising a microprocessor; first memory means coupled to said microprocessor for storing the program for the operation of said module to monitor and control one of said variables, said first memory means being releasably mounted in said module for the substitution thereof to permit the selection of the first memory means containing the program associated with the desired one of said variables; a second electrically alterable memory means coupled to said microprocessor for storing at least variable set point data for use in the control of said variable; manual input means coupled to said second memory means for selectively inputting said set point data to said second memory means; and interface means coupled to said microprocessor for at least receiving signals representative of sensor output and applying same to said microprocessor for effecting variable control.

2. The module as recited in claim 1, and including display means coupled to said microprocessor, said microprocessor being adapted to transmit signals to said display means for the selective effecting of display of the value of the sensor output signal, the stored set point data and the manually input set point data.

3. The module as recited in claim 2, wherein said first and second memory means are adapted to be nonvolatile upon the disconnection of power thereto.

4. The module as recited in claim 3, wherein said first memory means in an EPROM programmable outside of said module but not programmable by said microprocessor.

5. The module as recited in claims 2, wherein said manual input means is releasably mounted in said module for the substitution of said manual input means by a further manual input means adapted for association with the monitoring and control of a different variable.

6. The module as recited in claim 5, wherein said manual input means is adapted for the selective control of the operation of said module.

7. The module as recited in claims 2 or 5, wherein said interface means includes a plugable interface element defining a plurality of input and output channels and including switch means for the selection of the channels at which said received signals are received and said transmitted signals are transmitted.

8. The module as recited in claim 7, wherein said microprocessor means is adapted to receive control and set point data from selected channels of said interface means.

9. The module as recited in claim 7, wherein said microprocessor is adapted to transmit signals to at least one of said channels of said interface means representative of the value of sensor output suitable for supply to a recorder means.

10. The module as recited in claim 7, wherin said microprocessor is adapted to produce said signals for effecting variable control in the form of a series of pulses adapted to drive stepper motor means of a pump.

11. The module as recited in claim 2, adapted for the monitoring and control of a fermentation variable selected from the group including pH, dissolved oxygen, foam, agitation speed, air flow, pressure and temperature.

12. The module as recited in claim 2, wherein said display means is at least a numeric display means, and wherein said manual input means includes first switch means for selectively changing the value displayed in said display means and second switch means for actuating said microprocessor means to store said changed value for use in effecting control of said variable.

13. The module as recited in claim 12, wherein said first switch means includes at least first and second value changing switches for respectively raising and lowering the displayed digital value in said display means.

14. The module as recited in claim 13, wherein said first switch means includes third and fourth value changing switches, said first and third value changing switches being adapted to raise the displayed value in said display means at slow and fast rates respectively, said second and fourth value changing switches being adapted to lower the displayed value in said display means at slow and fast rates respectively.

15. The module as recited in claims 12, 13 or 14, wherein said set point data includes a set point profile comprising a set of elapsed process times and a variable value associated with each of said elapsed process times.

16. The module as recited in claim 15, wherein said second switch means includes a "delay" switch adapted to dispose said microprocessor so that said first switch means can change the display in said display means to a desired profile time delay for incorporation in said profile.

17. The module as recited in claim 15, wherein said second switch means includes a "remove" switch adapted to dispose said microprocessor so that said first switch means may change said display in said display means to a number representative of the time of a set point to be removed from said profile, whereby said selected set point is removed from said profile.

18. The module as recited in claim 15, wherein said second switch means includes an "add" switch adapted to dispose said microprocessor so that said first switch means sets a time value in said display representative of the time at which a set point is to be added to said profile and thereafter sets a set point value in said display means, whereby a set point of said value at said time is added to said profile.

19. The module as recited in claim 15, wherein said second switch means includes a "next" switch adapted to dispose said microprocessor so that said display means displays in sequence the time and the value of the next set point in said profile.

20. The module as recited in claim 15, wherein said second switch means includes an "exam" switch adapted to dispose said microprocessor so that said module displays in sequence first the time and then the value of each of the set points in said profile.

21. The module as recited in claim 20, wherein said first switch means is adapted to permit selective scrolling through said profile upon the actuation of said "exam" switch.

22. The module as recited in claim 15, wherein said second switch means includes an elapsed time switch adapted to dispose said microprocessor so that said display means displays the elapsed time of the process being controlled, said first switch means being adapted to change the displayed time and therefore the stored elapse time.

23. The module as recited in claim 15, wherein said second switch means includes a set switch adapted to dispose said microprocessor so that the then controlling set point value is displayed in said display, said displayed value and therefore the stored set point value being changeable by said first switch means.

24. The module as recited in claim 15, wherein said second switch means includes dead band switch means adapted to dispose said microprocessor so that said display means displays a value selectively set by said first switch means rrepresentative of a dead band about each said set point, said microprocessor being adapted to effect control only when the value of said variable as determined by said sensor output signal lies outside of said dead band.

25. The module as recited in claim 15, wherein said second switch means includes proportional switch means adapted to dispose said microprocessor so that said display means displays a value as determined by the operation of said first switch means representative of a maximum deviation in the variable at which maximum control is to be made by said microprocessor, selected from the group including the deviation of the value of the variable represented by the sensor output signal from the set point, the time during which said variable value represented by said sensor output signal deviates from the set point and the rate at which said variable value represented by said sensor output signal deviates from the set point, said microprocessor being adapted to effect control of said variable in proportion to the relationship between the deviation of said at least one type of deviation of said variable as represented by said sensor output signal to the stored maximum control deviation of said at least one type of deviation.

26. The module as recited in claim 25, wherein said microprocessor is adapted to effect control of said variable in proportion to the relationship between the deviation of said value and at least one of said deviation in time and said deviation in rate, as represented by said sensor output signal, to the stored maximum control deviation in value and to at least one of the stored maximum control deviations in time and rate, respectively, said proportional switch means being adapted to dispose said microprocessor so that said display means may display, at least sequentially, both said maximum value deviation and at least one of said maximum time and rate deviations.

27. The module as recited in claim 15, wherein said module includes alarm means and said second switch means includes alarm limit switch means adapted to dispose said microprocessor so that said display means displays at least one alarm limit value selectively set by said first switch means for storage by said microprocessor, said microprocessor being adapted to actuate said alarm means when the variable values represented by said sensor output signal is beyond said alarm limit value.

28. The module as recited in claim 15, wherein said variable is dissolved oxygen in a fermentation process, said second switch means being a response time switch adapted to dispose said microprocessor so that said display means may be set by said first switch means to a value representative of the response time of the associated sensor, said microprocessor being adapted to produce said signals for effecting control of said variable in response to said sensor output signals and in response to response time.

29. The module as recited in claim 15, wherein said variable is pH and said second switch means includes mixture time and add time switch means adapted to dispose said microprocessor so that said display means displays a mix time value and an add time value setable by said first switch means for storage by said microprocessor, said microprocessor being adapted to apply signals for effecting addition of acid or base in cycle increments as determined by said add time, the delay between cycle increments being determined by said mixt time.

30. The module as recited in claim 2, wherein said variable is controlled by the addition of measured amounts of a material, said manual input means including manual switch means adapted to dispose said microprocessor so as to transmit a signal representative of feeding of said material for so long as said manual switch means is actuated.

31. An apparatus for the monitoring and control of variables in a biochemical process comprising a housing; a conductive array mounted in said housing and defining a plurality of channels; power source means mounted in said housing and coupled to at least one channel of said array; sensor signal receiving means mounted in said housing and selectively couplable to at least a group of said channels, each said channel being associated with at least one sensor signal; control signal transmitting means mounted in said housing and selectively couplable to at least a group of said channels, each said channel being associated with at least one control signal; and a plurality of modules releasably mounted in said housing each associated with the control of a different variable; each said module including a microprocessor, memory means coupled to said microprocessor for storing the program for the operation of said module to monitor and control the associated variable and for storing at least variable set point data, manual input means coupled to said microprocessor for inputting at least said set point data, and interface means selectively couplable to at least a group of said channels of said conductive array for at least receiving sensor signals from at least one selected channel and transmitting control signals to at least one selected channel.

32. The apparatus as recited in claim 31, wherein said memory means includes at least a first memory means cooperating with said microprocessor for storing the program for the operation of said module and a second electrically alterable memory means for storing at least said variable set point data.

33. The apparatus as recited in claim 32, wherein said first and second memory means are adapted to be non-volatile upon the disconnection of power thereto.

34. The apparatus as recited in claim 33, wherein said first memory means is an EPROM programmable outside of said module but not programmable by said microprocessor.

35. The apparatus as recited in claim 32, wherein said first memory means is releasably mounted in said module for the substitution thereof, whereby said module may be adapted to monitor and control a different variable.

36. The apparatus as recited in claim 31, wherein each said module includes display means coupled to said microprocessor, said microprocessor being adapted to transmit signals to said display means for the selective effecting of display of the value of the sensor output signal, the stored set point data and the manually input set point data.

37. The apparatus as recited in claim 31, wherein said manual input means of at least one of said modules is adapted for the selective control of the operation of said module.

38. The apparatus as recited in claim 31, wherein said interface means includes a plugable interface element defining a plurality of input and output channels and including switch means for the selection of the channels at which said received signals are received and said transmitted signals are transmitted, said conductive array including means permitting the plugable interface element of at least a plurality of said modules to releasably connect with said conductive array to permit signal communication therebetween.

39. The apparatus as recited in claim 38, wherein said microprocessor means is adapted to receive control and set point data from selected channels of said interface means for storage in said memory means and for use in control of the associated variable.

40. The apparatus as recited in claim 39, wherein at least one of said modules is adapted to transmit control and set point data to at least one channel of said conductive array for receipt by another of said modules for use in control of the associated variable.

41. The apparatus as recited in claim 40, and including external computer interface means mounted in said housing and coupled to selected channels of said conductive array for application of control and set point data thereto and receipt of signals representative of sensor output therefrom.

42. The apparatus as recited in claim 31, wherein said sensor signal receiving means includes circuit means for conditioning sensor signals for transmission to said conductive array.

43. The apparatus as recited in claim 38, including recorder means mounted in said housing and couplable to channels of said conductive array; each said microprocessor being adapted to transmit signals to at least one of said channels of the associated interface means representative of the value of sensor output suitable for supply to said recorder means.

44. The apparatus as recited in claim 38, including pump means including a stepper driving motor, said microprocessor being adapted to produce said signals for effecting variable control in the form of a series of pulses adapted to drive said stepper motor pump means.

45. The apparatus as recited in claim 31, adapted for the monitoring and control of a plurality of fermentation variables selected from the group including pH, dissolved oxygen, foam, agitation speed, air flow, pressure and temperature, each of said modules being associated with one of said variables.

46. The apparatus as recited in claim 36, wherein said display means is at least a numeric means, and wherein said manual input means includes first switch means for selectively changing the value displayed in said display means and second switch means for actuating said microprocessor means to store said changed value for use in effecting control of said variable.

47. The apparatus as recited in claim 46, wherein said first switch means includes at least first and second value changing switches for respectively raising and lowering the displayed digital value in said display means.

48. The apparatus as recited in claim 47, wherein said first switch means includes third and fourth value changing switches, said first and third value changing switches being adapted to raise the displayed value in said display means at slow and fast rates respectively, said second and fourth value changing switches being adapted to lower the displayed value in said display means at slow and fast rates respectively.

49. The apparatus as recited in claims 46, 47 or 48, wherein said set point data includes a set point profile comprising a set of elapsed process times and a variable value associated with each of said elapsed process times.

50. The apparatus as recited in claim 49, wherein said second switch means includes a "delay" switch adapted to dispose said microprocessor so that said first switch means can change the display in said display means to a desired profile time delay for incorporation in said profile.

51. The apparatus as recited in claim 50, wherein said second switch means includes a "remove" switch adapted to dispose said microprocessor so that said first switch means may change said display in said display means to a number representative of the time of a set point to be removed from said profile, whereby said selected set point is removed from said profile.

52. The apparatus as recited in claim 49, wherein said second switch means includes an "add" switch adapted to dispose said microprocessor so that said first switch means sets a time value in said display representative of the time at which a set point is to be added to said profile and thereafter sets a set point value in said display means, whereby a set point of said value at said time is added to said profile.

53. The apparatus as recited in claim 49, wherein said second switch means includes a "next" switch adapted to dispose said microprocessor so that said display means displays in sequence the time and the value of the next set point in said profile.

54. The apparatus as recited in claim 49, wherein said second switch means includes an "exam" switch adapted to dispose said microprocessor so that said module displays in sequence first the time and then the value of each of the set points in said profile.

55. The apparatus as recited in claim 54, wherein said first switch means is adapted to permit selective scrolling through said profile upon the actuation of said "exam" switch.

56. The apparatus as recited in claim 49, wherein said second switch means includes an elapsed time switch adapted to dispose said microprocessor so that said display means displays the elapsed time of the process being controlled, said first switch means being adapted to change the displayed time and therefore the stored elapse time.

57. The apparatus as recited in claim 49, wherein said second switch means includes a set switch adapted to dispose said microprocessor so that the then controlling set point value is displayed in said display, said displayed value and therefore the stored set point value being changeable by said first switch means.

58. The apparatus as recited in claim 49, wherein said second switch means includes dead band switch means adapted to dispose said microprocessor so that said display means displays a value selectively set by said first switch means representative of a dead band about each said set point, said microprocessor being adapted to effect control only when the value of said variable as determined by said sensor output signal lies outside of said dead band.

59. The apparatus as recited in claim 49, wherein said second switch means includes proportional switch means adapted to dispose said microprocessor so that said display means displays a value as determined by the operation of said first switch means representative of a maximum deviation in the variable at which maximum control is to be made by said microprocessor, selected from the group including the deviation of the value of the variable represented by the sensor output signal from the set point, the time during which said variable value represented by said sensor output signal deviates from the set point and the rate at which said variable value represented by said sensor output signal deviates from the set point, said microprocessor being adapted to effect control of said variable in proportion to the relationship between the deviation of said at least one type of deviation of said variable as represented by said sensor output signal to the stored maximum control deviation of said at least one type of deviation.

60. The apparatus as recited in claim 59, wherein said microprocessor is adapted to effect control of said variable in proportion to the relationship between the deviation of said value and at least one of said deviation in time and said deviation in rate, as represented by said sensor ouput signal, to the stored maximum control deviation in value and to at least one of the stored maximum control deviations in time and rate, respectively, said proportional switch means being adapted to dispose said microprocessor so that said display means may display, at least sequentially, both said maximum value deviation and at least one of said maximum time and rate deviations.

61. The apparatus as recited in claim 49, wherein said module includes alarm means and said second switch means includes alarm limit switch means adapted to dispose said microprocessor so that said display means displays at least one alarm limit value selectively set by said first switch means for storage by said microprocessor, said microprocessor being adapted to actuate said alarm means when the variable values represented by said sensor output signal is beyond said alarm limit value.

62. The apparatus as recited in claim 61, and including said external alarm means coupleable to said conductive array each said microprocessor being adapted to transmit an alarm signal to said conductive array for transmission to said external alarm means when the variable value as represented by said senser output signal is beyond said alarm limit value.

63. The apparatus as recited in claim 49, wherein said variable associated with one of said modules is dissolved oxygen in a fermentation process, said second switch means of said one module being a response time switch adapted to dispose the associated microprocessor so that said display means may be set by said first switch means to a value representative of the response time of the associated sensor, said associated microprocessor being adapted to produce said signals for effecting variable control in response to said sensor output signals and said response time.

64. The apparatus as recited in claim 49, wherein said variable associated with one of said modules is pH and said second switch means of said module includes mixture time and add time switch means adapted to dispose the associated microprocessor so that said display means displays a mix time value and an add time value setable by said first switch means for storage by said microprocessor, said associated microprocessor being adapted to apply to said conductive array signals for effecting addition of acid or base in cycle increments as determined by said add time, the delay between cycle increments being determined by said mix time.

65. The apparatus as recited in claim 31, and including pump means in said housing coupled to said conductive array, one of said modules being adapted to control the associated variable by the addition of measured amounts of a material by said pump means, said manual input means of said one module including manual switch means adapted to dispose the associated microprocessor so as to transmit a signal representative of feeding of said material to said conductive array for transmission to said pump means for so long as said manual switch means is actuated.

66. The apparatus as recited in claim 49, wherein said set point data also includes events based set point data, the microprocessor of each module being adapted to transmit signals to the associated interface means for transmission to a channel of said conductive array for receipt by another of said modules, said signals being representative of the value of the sensor output signal associated therewith, the microprocessor of one module being adapted so that the transmission of said control signals are at least in part responsive to the value of sensor output signals transmitted by at least one other of said modules.

* * * * *